United States Patent [19]

Norris, Jr.

[11] 4,299,219
[45] Nov. 10, 1981

[54] INTRAVENOUS NEEDLE INSERTION DEVICE

[76] Inventor: George P. Norris, Jr., 10881 Snapper Creek Dr., North, South Miami, Fla. 33173

[21] Appl. No.: 104,042

[22] Filed: Dec. 17, 1979

[51] Int. Cl.³ .............................................. A61M 5/32
[52] U.S. Cl. .................................... 128/215; 128/297
[58] Field of Search ............... 128/215, 218 R, 218 A, 128/297–302

[56] References Cited

U.S. PATENT DOCUMENTS

| | | | |
|---|---|---|---|
| 7,341 | 5/1850 | Delluc | 128/302 |
| 1,934,046 | 11/1933 | Demarchi | 128/215 |
| 2,103,174 | 12/1937 | Posada | 128/215 |
| 2,743,723 | 5/1956 | Hein | 128/215 |
| 2,945,496 | 7/1960 | Fosdal | 128/297 |
| 3,122,138 | 2/1964 | Geary | 128/215 |
| 3,561,448 | 2/1971 | Peternel | 128/334 C |
| 3,727,614 | 4/1973 | Kniazuk | 128/218 A |

Primary Examiner—Dalton L. Truluck
Attorney, Agent, or Firm—Ernest H. Schmidt

[57] ABSTRACT

A transparent vacuum cylinder has an open end adapted for placement in sealing engagement over the skin of a patient at a zone where venipuncture is to be performed, and a vacuum drawing syringe communicating therewith for establishing a vacuum serving to draw the skin and underlying vein partially into the vacuum chamber, where the vein will become engorged with blood to facilitate needle insertion. An intravenous needle holding and manipulating assembly coaxially arranged within the vacuum cylinder and hermetically sealed with respect thereto includes releaseable mechanism at the open, inner end of the vacuum cylinder for temporarily supporting an intravenous needle and manual grasping means at the other end to permit manipulation of the needle for insertion in the distended vein while under vacuum.

8 Claims, 3 Drawing Figures

INTRAVENOUS NEEDLE INSERTION DEVICE

This invention relates to venipuncture and is directed particularly to a device for the insertion of an intravenous needle or cannula under vacuum.

Ordinarily, intravenous needles used for injecting blood, volume increasing fluids, feeding fluids, medications, blood transfusions and the like are inserted directly into the vein by hand. Under certain pathological or traumatic conditions, particularly when blood pressure is unusually low, veins lying close to the skin, such as at the inside of the arm and at the wrist and ankle are substantially collapsed, making it difficult, if not impossible, to find the lumen upon direct insertion and manipulation of the needle or cannula. This condition is especially critical when a patient is in shock due to excessive bleeding or internal hemorrhaging. If a licensed physician is in attendance, the emergency procedure known as a leg vein "cut-down" can be resorted to, exposing the ankle vein to permit surgical cutting and direct insertion of the needle. However, in many emergency situations in which a patient is in shock because of excess hemorrhaging, a paramedic is first to arrive at the scene to offer medical treatment. This is particularly true in the case of automobile and industrial machine accidents resulting in severe injuries to the patient. Since a paramedic is not authorized to perform a surgical "cut-down" procedure, he must, under such emergency conditions, use his best skills to manually insert an intravenous needle into the lumen of a vein, even though it is in a collapsed or partially collapsed condition due to low blood pressure, an extremely difficult task. It is, accordingly, the principal object of this invention to provide an intravenous needle insertion device which will locally distend or expand a small length of blood vessel, at the inside of the arm for example, by filling it with blood, and thereby facilitate the insertion of the tip of an intravenous needle precisely within the lumen so that intravenous fluids can be administered without life-threatening delay.

A more practical object of the invention is to provide an intravenous needle insertion device of the character described wherein an increase in size of the vein section selected for venipuncture is accomplished by subjecting the localized area of the overlying skin to a partial vacuum causing the collapsed vein section to become engorged with venous blood.

Yet another object of the invention is to provide an intravenous needle insertion device of the character described including a transparent vacuum cylinder having an open end adapted for placement in sealing engagement over the skin of a patient at a zone where venipuncture is to be performed, a vacuum drawing syringe communicating with the vacuum cylinder and operative to draw the skin and underlying vein partially into the vacuum chamber, and an intravenous needle holding and manipulating assembly within the vacuum cylinder, hermetically sealed with respect thereto and having releasable mechanism for temporarily supporting an intravenous needle for manipulation from the outside to insert it into the engorged vein section while under vacuum.

A further object of the invention is to provide an intravenous needle insertion device of the character described which will be simple construction, easy to use, dependable in operation and durable.

Other objects, features and advantages of the invention will be apparent from the following description when read with reference to the accompanying drawings. In the drawings, wherein like reference numerals denote corresponding parts throughout the several views.

Figure 1:
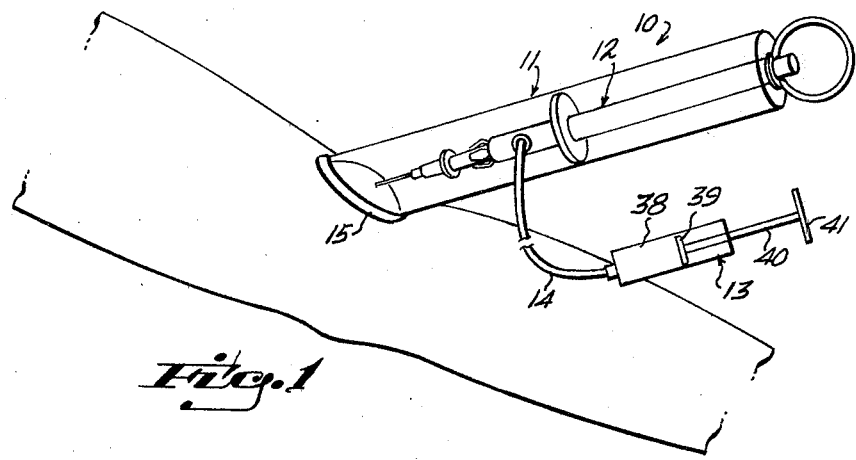
FIG. 1 is an intravenous needle insertion device embodying the invention, shown in use.
Figure 2:
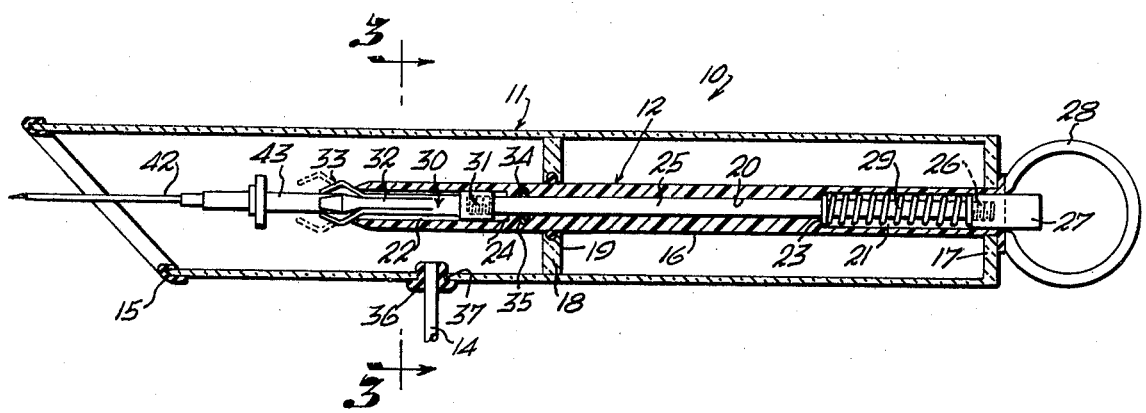
FIG. 2 is a longitudinal cross-sectional view of the intravenous insertion device, shown separately.
Figure 3:
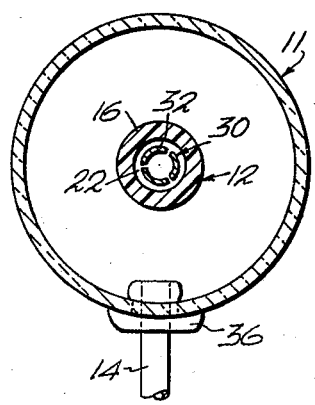
FIG. 3 is a transverse cross-sectional view of the device, taken along the line 3—3 thereof in the direction of the arrows.

Referring now in detail to the drawings, reference numeral 10 in FIGS. 1 and 2 designates, generally, a preferred form of intravenous needle insertion device embodying the invention. As illustrated, the device comprises a vacuum cylinder 11, intravenous needle holding and manipulating assembly 12 coaxially arranged within said cylinder, and a vacuum drawing syringe 13 communicating with a lower end portion of vacuum cylinder 11 by a length of flexible, non-collapsible tubing 14.

The lower end of the vacuum cylinder 11 is cut at an angle of approximately 45 degrees and, as best illustrated in FIG. 2, is fitted with a replaceable, soft rubber gasket 15, preferably of surgical rubber, to facilitate the establishment of an air-tight seal against the skin of the patient in use of the device, as is hereinafter more particularly described. The vacuum cylinder 11, moreover, is fabricated of a transparent material, such as of an acrylic resin plastic, so that manipulative insertion of the intravenous needle during use of the device can be visually observed.

As best illustrated in FIG. 2, the intravenous needle holding and manipulating assembly 12 comprises an elongated tubular member 16 coaxially arranged within the vacuum cylinder 11. The upper end of the elongated tubular member 16 projects through the upper end of the vacuum cylinder 11, and is slidingly supported with respect thereto by means of an annular guide member 17. The lower end portion of the elongated tubular member 16 is similarly constrained in coaxial relation within vacuum cylinder 11 by means of an annular partition member 18. The inner periphery of the annular partition member 18 is grooved to receive an o-ring gasket 19 serving to hermetically seal the outer peripheral surface of elongated tubular member 16 with respect to vacuum cylinder 11.

The elongated tubular member 16 comprising needle holding and manipulating assembly 12 will preferably be fabricated of a tough synthetic plastic material, and is formed with central bore 20 the upper and lower ends of which extend into increased diameter bore portions 21 and 22, respectively, defining respective upper and lower internal annular shoulder portions 23 and 24. Received for reciprocative sliding motion within the elongated tubular member 16 is a cylindrical plunger rod 25, the upper end of which is externally threaded, as indicated at 26, for the screw-threaded attachment of an internally-threaded, cylindrical push-button 27. Push-button 27 extends freely through finger control ring 28 secured with respect to the outer end of tubular member 16. A helical compression spring 29 circumjacent an upper end portion of plunger rod 25 is constrained between annular shoulder 23 and the annular underside of push-button 27, and serves to resiliently urge said plunger rod in the upper or withdrawn position within the elongated tubular member 16.

The lower end of plunger rod 25 has attached thereto a coaxiallyextending chuck member 30 having an increased diameter, cylindrical head portion 31 extending outwardly of which is a plurality, three in the embodiment illustrated, of peripherally-spaced spring fingers 32. The outer ends of these spring fingers project from the lower end of the elongated tubular member 16, whereat they are outwardly and then inwardly bent to define arcuate claw portions 33. The claw portions 33 are circularly arranged for grasping and holding the head of an intravenous needle, as is hereinafter more particularly described. In this connection, it is to be understood that the helical compression spring 29 is of sufficient strength normally to effect relative inward movement of the claw portions 33 of chuck member 30 by virtue of outside portions being cammed against the inner peripheral edge at the inner end of the elongated tubular member 16. In such withdrawn position, head portion 31 of chuck member 30 is spaced from annular shoulder 24. A second o-ring 34 seated in annular groove 35 and embracing the outer peripheral surface of plunger rod 25 serves to hermetically seal the upper open end of elongated tubular member 16 with respect to the vacuum producing end of vacuum cylinder 11.

As best illustrated in FIG. 2, the flexible tubing 14 is connected at one end with the interior of the lower vacuum forming portion of the vacuum cylinder 11 by means of an annular, surgical rubber plug 36 securely fitted within circular opening 37 in said vacuum cylinder. The other end of the non-collapsible length of tubing 14 (see FIG. 1) communicates with the lower end of the cylinder 38 of vacuum syringe 13. A piston 39 slidingly fitted within the cylinder 38 is joined with an outwardly-extending actuating rod 40 terminating in a cross-bar 41 by means of which the piston may be withdrawn for the purpose of establishing a temporary vacuum within the lower end portion of vacuum cylinder 11, in the manner and for the purpose now to be described.

In use of the intravenous needle insertion device, a standard intravenous needle or cannula 42 of the type having a clear plastic connecter head 43 is first secured to the chuck member 30 so as to be securely held in coaxial alignment with intravenous needle holding and manipulating assembly 12. This is readily accomplished by depressing push-button 27 so that the claw portions 33 of spring fingers 32 will open outwardly to permit insertion of needle connector head 43, as illustrated by the broken-line representation of said claw portions in FIG. 2. It will be understood that upon release of the push-button 27, the claw portions 33 will be urged together in embracing relation about the needle connecter head to hold it securely in place, as illustrated by the full-line representation thereof in FIG. 2. After attachment of the needle as described above, finger ring 28 will be used to withdraw the intravenous needle holding and manipulating assembly 12 so that the tip of the needle is well within the open end of vacuum cylinder 11. The inclined lower end opening of the vacuum cylinder 11 will then be placed in contact with the skin of the patient surrounding the zone of the vein to be pierced (see FIG. 1). The actuating rod 40 of the vacuum syringe 13 will then be withdrawn from its lowermost position to pull a vacuum in the lower end of vacuum cylinder 11, whereupon the skin and underlying vein to be pierced will be drawn upwardly to a slight degree into the lower end of said vacuum cylinder 11. This localized distension of the skin and underlying vein causes engorgement by venous blood into that area of the vein, to such an extent as facilitates successful needle insertion. The vacuum cylinder 11 and the intravenous needle holding and manipulating assembly 12 can be adjusted to accurately push the needle forward into the blood-filled vein, as observed through the transparent vacuum cylinder. In this connection, it will be understood that there will be sufficient space between the needle head grasping claw portions 33 to permit observation of a successful venipuncture by the appearance of blood in the "flash chamber" of said needle head. Having thus completed needle insertion, the needle release pushbutton 27 will be depressed, whereupon the insertion device can be removed, leaving the needle in place for connection with tubing, syringes or the like for the injection of life supporting fluids or medications.

While I have illustrated and described herein only one form in which my invention can conveniently be embodied in practice, it is to be understood that this embodiment is presented by way of example only and not in a limiting sense. My invention, in brief, comprises all the modifications and embodiments coming within the scope and spirit of the following claims.

What I claim as new and desire to secure by Letters Patent is:

1. An intravenous needle insertion device comprising, in combination, a peripheral wall defining an elongated vacuum chamber open at one end, an elongated intravenous needle holding and manipulating assembly co-axially disposed within said vacuum chamber, means supporting said intravenous needle holding and manipulating assembly for relative axial movement within said vacuum chamber, said needle holding and manipulating assembly comprising releasable means for holding a headed intravenous needle in coaxial alignment therewith so that the needle tip extends in the direction of said vacuum chamber opening, means hermetically sealing the needle holding end portion of said needle holding and manipulating assembly with respect to a portion of the vacuum cylinder, adjacent the open end thereof and means for creating a vacuum in said open end portion of said vacuum cylinder whereat said open end is sealed off by reason of said opening being pressed into contact with the skin of the patient surrounding the vein to be punctured, said needle holding and manipulating assembly further comprising mechanism controlling said releasable means for releasing a held intravenous needle from the outside of said vacuum cylinder while said vacuum cylinder is being pressed into contact with the skin of the patient.

2. An intravenous needle insertion device as defined in claim 1 wherein said elongated vacuum chamber comprises a transparent cylindrical tube and wherein said releasable headed intravenous needle holding means comprises a tubular member reciprocatively fitted within which is a cylindrical plunger rod, yieldable means normally urging said plunger rod in a first, outward limit position with respect to said tubular member, needle head grasping means at the vacuum cylinder open end of said tubular member operative, upon said plunger rod being moved to a second position with respect to said tubular member, to open said needle grasping means to permit insertion for grasping of a headed needle, and manual grasping means at the opposite end of said elongated tubular member to provide for in and out relative movement of said intravenous needle holding and manipulating assembly with respect to said cylindrical tube.

3. An intravenous needle insertion device as defined in claim 2 wherein said hermetically sealing means comprises an o-ring gasket in interfitting contact between an exterior peripheral wall portion of said plunger rod and an interior peripheral wall portion of said elongated tubular member, and a second o-ring in interfitting contact between an outer peripheral wall portion of said elongated tubular member and an annular closure member circumjacent said elongated tubular member and an inner peripheral wall portion of said cylindrical vacuum cylinder.

4. An intravenous needle insertion device as defined in claim 2 wherein said vacuum creating means comprises a vacuum drawing syringe and conduit means communicating between said vacuum drawing syringe and said open end portion of said vacuum cylinder.

5. An intravenous needle insertion device as defined in claim 4 wherein said hermetically sealing means comprises an o-ring gasket in interfitting contact between an exterior peripheral wall portion of said plunger rod and an interior peripheral wall portion of said elongated tubular member, and a second o-ring in interfitting contact between an outer peripheral wall portion of said elongated tubular member and an annular closure member circumjacent said elongated tubular member and an inner peripheral wall portion of said cylindrical vacuum cylinder.

6. An intravenous needle insertion device as defined in claim 5 wherein the peripheral edge of the open end of said vacuum chamber lies in a plane oblique with respect to the lonitudinal axis of said cylindrical vacuum chamber.

7. An intravenous needle insertion device as defined in claim 6 including a relatively soft, resilient gasket secured to said open end peripheral edge.

8. An intravenous needle insertion device as defined in claim 6 wherein said needle head grasping means comprises plurality of spring fingers, each spring finger terminating in an arcuately bent claw portion operative to embracingly grasp the head of an intravenous needle.

* * * * *